United States Patent
Zaharia Czeizler

(10) Patent No.: US 6,274,158 B1
(45) Date of Patent: Aug. 14, 2001

(54) TREATMENT WITH RECOMBINANT HUMAN ERYTHROPOIETIN OF BLEEDING IN PATIENTS WITH NORMAL AND ABNORMAL HEMOSTASIS

(76) Inventor: Veronica L. Zaharia Czeizler, 237 E. 20$^{th}$ St., New York, NY (US) 10003

( * ) Notice: Subject to any disclaimer, the term of this patent is extended or adjusted under 35 U.S.C. 154(b) by 0 days.

(21) Appl. No.: 09/335,076

(22) Filed: Jun. 17, 1999

Related U.S. Application Data

(63) Continuation-in-part of application No. 09/018,815, filed on Feb. 4, 1998, now Pat. No. 5,951,996
(60) Provisional application No. 60/091,598, filed on Jul. 2, 1998, and provisional application No. 60/125,253, filed on Mar. 19, 1999.

(51) Int. Cl.$^7$ .............................. A61F 2/02; C07K 14/505
(52) U.S. Cl. ............................................. 424/423; 530/350
(58) Field of Search ............................................. 424/423

(56) References Cited

U.S. PATENT DOCUMENTS 6,011,000 * 1/2000 Perrine et al. ........................... 514/2

* cited by examiner

*Primary Examiner*—Carlos A. Azpuru
(74) *Attorney, Agent, or Firm*—Gottlieb, Rackman & Reisman, P.C.

(57) ABSTRACT

Recombinant human Erythropoietin is used in a method as a hemostatic agent for the treatment or prevention of bleeding from any organ or body part involved with benign or malignant lesions, surgical traumatic, non-healing/difficult to treat lesions, or radiation injury. The method can control or prevent the bleeding in patients with congenital or acquired disorders of coagulation, platelets, or blood vessels, patients on therapeutic or overdose of anticoagulants or antiplatelet drugs. The method consists of the subcutaneous, intravenous or oral administration of recombinant human Erythropoietin for the purpose of preventing or stopping bleeding.

35 Claims, No Drawings

US 6,274,158 B1

TREATMENT WITH RECOMBINANT HUMAN ERYTHROPOIETIN OF BLEEDING IN PATIENTS WITH NORMAL AND ABNORMAL HEMOSTASIS

This application is a continuation-in-part of Ser. No. 09/018,815, filed Feb. 4, 1998, now U.S. Pat. No. 5,951,996 and claims priority of provisional applications 60/091,598 filed Jul. 2, 1998, and 60/125,253 filed Mar. 19, 1999.

FIELD OF THE INVENTION

This invention relates to a new use for recombinant human Erythropoietin. It further relates to hemostatic agents (agents that promote the mechanisms for stopping bleeding) in patients with normal hemostasis as well as in patients with abnormal hemostasis. The invention further relates to methods for controlling or preventing bleeding from any organ or part of the body.

BACKGROUND OF THE INVENTION

Recombinant human Erythropoietin (also known as Procrit or Epoetin or Epogen) is a glycoprotein hormone, thought to be produced primarily in the kidneys and to a lesser extent in the liver. It is a stimulating factor for erythropoiesis, the process by which erythrocytes (red blood cells) are formed. Human recombinant human Erythropoietin has been produced by recombinant technology, and is known as Epoetin.

Recombinant human Erythropoietin is primarily used to induce production of red blood cells to combat anemia. It is used in the treatment of anemia of chronic renal failure, anemia of cancer and in HIV positive patients. The prior art is not aware of the use of Recombinant human Erythropoietin to control bleeding or to prevent rebleeding.

Recombinant human Erythropoietin has been used successfully in the treatment of advanced gastrointestinal cancer to increase the Hemoglobin/Hematocrit (Hgb/Hcrt) count by stimulation of red blood cell production. Its effect on stopping or preventing gastrointestinal bleeding has not been recognized. ("Recombinant human Erythropoietin Beta in the Treatment of Anemia in Patients with Advanced Gastrointestinal Cancer" J. Clin. Oncology 16, No. 2, February 1998 p. 434–40).

In uremic patients, it is known that Recombinant human Erythropoietin corrects the prolonged bleeding time after one week of treatment and increases the Hemoglobin/Hematocrit after two weeks of treatment. But this information has not been previously considered as related to the problem of stopping or preventing the bleeding in an actual uremic or non-uremic patient. An enhanced platelet aggregation in response to Ristocetin was noted in Recombinant human Erythropoietin treated patients, which correlated with the rise in platelet Serotonin. These facts explain the improved platelet subendothelial cell interaction and the shortening of the bleeding time, found in Recombinant human Erythropoietin treated uremic patients. Recombinant human Erythropoietin also boosts the coagulation mechanism. This is achieved by decreasing the protein C and S and anti-thrombin III (which are natural anticoagulants), in uremic patients treated with Recombinant human Erythropoietin. But this observation has never been translated into using Recombinant human Erythropoietin in a bleeding patient with normal or abnormal coagulation mechanism in order to limit the bleeding.

BRIEF DESCRIPTION OF THE INVENTION

This invention is a further improvement on my earlier patent application, 09/018,815, filed Feb. 3, 1998, for "Treatment of Chronic Diffuse Gi Bleeding with Erythropoietin." That invention was based upon research primarily with patients who had diffuse gastrointestinal bleeding. The present invention is an expansion of that investigation which has unexpectedly resulted in a method for the treatment of many different bleeding disorders.

Recombinant human Erythropoietin is administered to stop or prevent the bleeding from any part of the body involved with benign or malignant lesions, surgical, traumatic or difficult to heal lesions, in patients being naturally or therapeutically anti-coagulated, patients with bleeding disorders related to their coagulation mechanism, blood vessels or platelets, or patients on antiplatelet drugs. This effect is dependent on the dose and the frequency of administration of Recombinant human Erythropoietin. It occurs regardless of the HIV status of the patients. This "hemostatic effect" is due to the fact that Recombinant human Erythropoietin can boost the mechanisms involved in hemostasis. Patients with recurrent bleeding which failed several local surgical and non-surgical attempts to stop the bleeding, who need transfusions of blood products and repeated hospitalizations have a major decline in the quality of their life. It is in these difficult or impossible to treat bleeding conditions, that Recombinant human Erythropoietin administered preferably by subcutaneous route, stops and prevents rebleeding in just a few days, making surgery, transfusions of blood products or hospitalizations unnecessary. There is a major improvement in the quality of life of these patients, with substantial savings in healthcare cost.

The population to whom this invention is addressed are patients with bleeding from benign or malignant lesions anywhere in the body or from any organ. Bleeding traumatic, surgical or difficult to treat wounds are suitable to be treated. Control or prevention of bleeding can be achieved in patients who have a normal or abnormal hemostatic mechanism. Examples of patients with an abnormal hemostatic mechanism are as follows: patients with abnormal coagulation parameters due to therapeutic anticoagulation, or due to congenital or acquired coagulation abnormality; patients with a prolonged bleeding time due to low platelet count, a functional platelet abnormality or due to antiplatelet drugs; patients with a blood vessel abnormality; or patients with a combination of the above mentioned disorders.

The present invention comprises the administration of Recombinant human Erythropoietin preferably subcutaneously, but also intravenously or orally, depending on the case. The invention results in the prevention or disappearance of clinical evidence of bleeding with an increase or stabilization of the Hemoglobin/Hematocrit (Hgb/Hcrt) and no further need for transfusion of blood products or hemostatic surgical or nonsurgical procedures. Recombinant human Erythropoietin can be used in the bleeding patient as a hemostatic agent. The rapidity and the degree of control of the bleeding process, depends on the dose and the frequency of administration of Recombinant human Erythropoietin.

The process of the invention comprises: 1). During the "initial treatment" the patients are administered daily high doses of Recombinant human Erythropoietin for about 1–2 weeks. If the bleeding is under control they are treated on a 2) "maintenance treatment" during which they are treated at much lower doses ,2–3 times per week. Thereafter if the bleeding continues to be completely controlled, they are switched to a 3) "long-term maintenance treatment". This phase of the treatment consists of very low doses of Recombinant human Erythropoietin administered weekly, biweekly, or once a month, for several months. 4) If no bleeding occurs during this time, the patient is monitored closely for months or years; no Recombinant human Erythropoietin is administered during this "long term follow up" period.

In the 10 examples presented below, Recombinant human Erythropoietin (1) stopped the bleeding in all 10 patients treated (2) no further transfusions of blood products were needed, thereby avoiding the complications of repeated transfusions, (3) the treatment can be done on an outpatient basis (4) without the need for repeated surgical/nonsurgical hemostatic procedures (5) Recombinant human Erythropoietin can be used to control or prevent bleeding in patients with a bleeding tendency (abnormal hemostatic mechanism), an effect which depends on the dose and frequency of administration (6) the patient's quality of life undergoes a major improvement, (7) no side effects were noted (8) there was a major saving for the patient as well as for the healthcare industry (9)Recombinant human Erythropoietin can be used to prevent excessive blood loss in invasive procedures where the risk of excessive bleeding is high, due to the patient's hemostatic parameters, the nature of surgery or the local anatomy.

DETAILED DESCRIPTION OF A PREFERRED EMBODIMENT

The invention is appropriate for the treatment or prevention of severe bleeding, sometimes recurrent, failing every attempt at local hemostasis and transfusion of red blood cells, platelets or coagulation factors. The bleeding can occur from benign, malignant, surgical, traumatic or difficult to heal lesions, of any body part or organ, during organ transplant or skin grafting, regardless of the HIV status of the patient and even in the presence of a bleeding disorder. The list of bleeding disorders can include: disorders of coagulation, decreased platelet count, disorders of platelet function, disorders of the blood vessels, patients on anticoagulants or antiplatelet drugs. (For a detailed list see Table no 1.) In all the above conditions, Recombinant human Erythropoietin proves its efficacy as a hemostatic agent. The rapidity and degree of control of the bleeding process depends on the dose and frequency of administration of Recombinant human Erythropoietin.

The treatment of a bleeding patient with Recombinant human Erythropoietin can be broken down into four phases, of progressively decreasing doses and frequency of administration of the drug.

Following is a presentation of the concept behind each phase and a detailed outline of doses and frequency of administration.

The "initial treatment" with Recombinant human Erythropoietin in a bleeding patient, is administered for the purpose of stopping the bleeding, boosting the red blood cell production and decreasing future transfusion requirements. Recombinant human Erythropoietin is administered at high doses, daily, depending on the severity of the bleeding. After 1–2 weeks, when the bleeding is controlled (no clinical evidence of bleeding, stable Hemoglobin/Hematocrit), the patient may be continued on: "maintenance treatment".

During the "maintenance treatment" much lower doses of Recombinant human Erythropoietin are administered 2–3 times per week. After a few weeks, if bleeding does not recur, the patient is switched to:

"Long-term maintenance treatment" at very low doses of Recombinant human Erythropoietin, administered weekly, biweekly, every 3 weeks, or once a month.

An attempt can be made to stop the Recombinant human Erythropoietin completely, after which the patient is observed clinically for evidence of rebleeding and the Hg/Hcrt is monitored, during the "long term follow up". After the treatment is initiated in accord with this invention, no further transfusion is needed, although bleeding and some drop in Hgb/Hcrt may recur, if Recombinant human Erythropoietin treatment is dropped completely. Complete disappearance of these symptoms occurs upon restarting Recombinant human Erythropoietin (for more details of the treatment method see claims).

Example no. 1 is an 88 years old female with deep venous thrombosis and pulmonary embolus on Heparin and Warfarin anticoagulation and Aspirin as antiplatelet drug. The patient developed a massive retroperitoneal bleeding, and a critically low Hemoglobin. The bleeding continued for several days despite stopping the Heparin, and massive red blood cell and fresh frozen plasma (coagulation factors) transfusions. The bleeding occurred at a much faster rate than our capacity to transfuse blood. The patient developed a moderate degree of renal failure (Creatinine of 3.8) further worsening the platelet function and hence the bleeding tendency. The bleeding only stopped after Vitamin K was administered to completely revers the anticoagulation, and the aspirin was held. The patient developed a severe myocardial infarction, with cardiac failure and life threatening arrhythmias. In order to save the patient's life, Heparin and Aspirin had to be restarted, as standard treatment of an acute myocardial infarction. Later on, Warfarin was added too. In an attempt to prevent reoccurrence of the retroperitoneal bleeding Recombinant human Erythropoietin was started at 5,000 units subcutaneously daily. No further recurrence of the retroperitoneal bleeding or drop of Hemoglobin were noted over the subsequent days despite continued anticoagulation (with Heparin and Warfarin) and antiplatelet medication(Aspirin). For two days the PT, PTT, INR (coagulation parameters) were several times the target value, which during a previous experience led to massive bleeding. The Recombinant human Erythropoietin was increased to 7,000 units per day administered subcutaneously. During those 2 days there was a slight decrease in Hemoglobin from 12 to 10.4 after which it remained stable. The Recombinant human Erythropoietin was decreased to 7,000 units three times a week. The Hemoglobin increased to 13 over the following 2 weeks despite continuous anticoagulation and antiplatelet medication. Subsequently the Recombinant human Erythropoietin was stopped. No side effects were noted.

Example no. 2: is a 65 year old male treated in accord with the present invention. The patient had a history of radiation proctitis secondary to radiotherapy for a prostate cancer, with a string of hospital admissions for critically low Hemoglobin/Hematocrit and packed red blood cell transfusions prior to the initiation of Recombinant human Erythropoietin. When first seen in consultation during one of his hospital admissions, his Hemoglobin was 3.5, Hcrt-12.2 and MCV 65. During the 6 weeks preceding the initiation of Recombinant human Erythropoietin, 20 units of packed red blood cells were transfused. A repeat colonoscopy revealed diffuse angioectasia (dilation of the small blood vessels) of the recto-sigmoid mucosa and diffuse erosions and oozing of blood, consistent with radiation proctitis. Courtenemas were unsuccessful in stopping the bleeding.

Recombinant human Erythropoietin 5,000 units three times a week was started. After the first week of treatment, the bleeding completely stopped. No further transfusion was needed, the patient's bleeding stopped and he felt better. The patient however did not follow the recommended treatment. Eventually his Hemoglobin dropped to 6.5 and he returned. The patient came once every one-two weeks and later on every three weeks at which time recombinant human Erythropoietin 5,000 units were administered subcutaneously. During the time when he was off Recombinant human Erythropoietin for several weeks, his Hgb dropped to about 7.0 and he had rectal bleeding, After Recombinant human Erythropoietin was restarted, the rectal bleeding disappeared and the Hgb/Hcrt increased to 12.5. To this date, no packed red blood cells were transfused after Recombinant human Erythropoietin had been started. No side effects were noted.

Example no. 3: was an 84 year old male with multiple hospital admissions for lower gastrointestinal bleeding and severe symptomatic iron deficiency anemia. For the previous two years he was admitted every two months for packed red blood cell transfusion of an average of 4 units. He was seen in consultation during one admission for hematochesia (rectal bleeding) and a Hemoglobin of 9.0. A colonoscopy revealed diffuse colonic angiodysplasia. He was started on Recombinant human Erythropoietin 4,000 units three times a week which he received for two weeks, followed by 4,000 units two times a week for two months after which he was maintained on 2,000 units once or twice a week, then 3,000 units once a week. His Hemoglobin has increased from 9.0 to 13.0. Following the treatment as recommended, no transfusion of packed red blood cells has been used since Recombinant human Erythropoietin was initiated. His Hemoglobin remained between 12.0 and 13.0 for the subsequent year with no clinical evidence of bleeding. No side effects were noted.

Example no. 4: is a 69 year old female, with a history of cancer of the rectum and the perirectal area, who had resection of the tumor followed by chemotherapy and radiotherapy. She had a history of several weeks of rectal bleeding. Five and a half months prior to the initiation of Recombinant human Erythropoietin her Hemoglobin/Hematocrit were 6.9/20.9 and she was transfused 2 units of packed red blood cells. Two weeks later, her Hgb/Hcrt were 7.7/24.6 and 4 units of packed red blood cells were transfused. Ten days later, she was transfused another 2 units of packed red blood cells. Recombinant human Erythropoietin 5,000 units subcutaneously for 3 days was started, while in the hospital after which she was discharged home. As an outpatient, she came to the office every 1–2 weeks for chemotherapy therapy with 5 FU and Leucovorin. At the same time she received Recombinant human Erythropoietin 2,000 units subcutaneously. The rectal bleeding stopped completely after the third dose of Recombinant human Erythropoietin. Two months later, the patient was transfused 2 units of packed red blood cells. The very low dose of Recombinant human Erythropoietin, 2,000 units every 1–2 weeks kept the patient free of transfusions for 7 weeks. Whereas during the month prior to starting Recombinant human Erythropoietin, 8 units of packed red blood cells were transfused. It is presumed that higher doses and more frequent administration would have kept the patient entirely transfusion free. No side effects were noted.

Example no. 5: is a 74 year old female with a one and a half year old history of vaginal bleeding due to adenocarcinoma of the endometrium. Due to metastasis, hysterectomy was not performed and chemotherapy and radiotherapy were administered. She developed deep venous thrombosis of the left femoral vein ,for which she received therapeutic doses of Heparin and later on Warfarin (both anti-coagulants). With a Hemoglobin of 9, fully anticoagulated she had active vaginal bleeding . Recombinant human Erythropoietin subcutaneously was started at 2,000 units 3 times per week. During the second week of Recombinant human Erythropoietin treatment, the vaginal bleeding stopped and her Hgb remained stable at 9.5 for the following 10 months. No side effects were noted.

Example no. 6: is a patient with end-stage renal disease on hemodialysis, liver insufficiency due to cirrhosis of the liver with a PT and PTT one and a half times normal for many months and a prolonged bleeding time due to chronic renal failure. He developed severe epistaxis (nose bleeding) which would not stop for several days. He was admitted to the hospital, requiring several units of packed red blood cells transfused. Nasal packing was done, but after removal of the packing the bleeding continued. This sequence of events repeated several times. The patient was for a long time on 10,000 units of Recombinant human Erythropoietin given intravenously 3 times a week for anemia due to chronic renal failure. In view of the continued bleeding, the Recombinant human Erythropoietin was increased from 10,000 units 3 times a week intravenously to 15,000 units daily subcutaneously. Soon the epistaxis completely stopped and remained so for the following months. Later on, Recombinant human Erythropoietin was decreased to its original dose of 10,000 units 3 times a week given intravenously without recurrence of bleeding and the patient was discharged home. No side effects were noted.

Example no. 7: is a 67 year old female with a history of breast cancer in remission for several years. She underwent revision of femoropopliteal bypass surgery graft of the left lower extremity. She was on anticoagulation and antiplatelet medication (Aspirin) for a coexisting cardiac disease. Several weeks following her surgery, the surgical wound was still not closed and a serosanguinous discharge was leaking from the open wound. Recombinant human Erythropoietin 2,000 units sub-cutaneously 2 times a week led to decrease and then complete resolution of the serosanguinous leakage. Recombinant human Erythropoietin was stopped. Surgical manipulation of the improperly/incompletely closed surgical incision site led to recurrence of bloody fluid leakage. Restarting the Recombinant human Erythropoietin treatment at the same dose as before led to a stop of the oozing of the bloody fluid. No side effects were noted.

Example no. 8: is an 84 year old male with recurrent bleeding due to angiodysplasia of the colon, with severe anemia, required multiple hospital admissions and blood transfusions despite oral iron supplementation. After being started on outpatient Recombinant human Erythropoietin, his stools became free of blood and no transfusion of packed red blood cells was required over the ensuing 18 months of follow up. On a maintenance dose of 4,000 units per week and later on 4,000 units every 2–3 weeks, his Hemoglobin remained stable at around 12 and there was no clinical evidence of bleeding. No side effects were noted.

Example no. 9: is an elderly female with recurrent melaena due to angiodysplasia of the duodenum. The patient was therapeutically anticoagulated for a valvular heart disease. Despite oral iron supplementation and repeated endoscopic attempts to stop the bleeding she required frequent packed red blood cell transfusions for critically low Hemoglobin/Hematocrit (6.5/19). Following multiple transfusions, the patient developed an autoimmune hemolytic anemia, and her transfusion requirements increased. After Recombinant human Erythropoietin was started her stools became negative for occult blood and repeat endoscopies failed to show any bleeding. She was maintained on recombinant human Erythropoietin, 10,000 units three times a week. No side effects were noted.

Example no. 10: was a patient with endometrial cancer invading the pelvic organs such as the vagina, bladder and rectum, who had massive, recurrent rectal bleeding with critically low Hemoglobin/Hematocrit, necessitating repeated transfusions of blood products. The patient was concomitantly on Warfarin anticoagulation for a deep venous thrombosis. Due to a lack of metabolization of warfarin she became over anticoagulated (her coagulation parameters were 4 times the target value for anticoagulation). Repeated transfusions of fresh frozen plasma (containing the coagulation factors) and Vitamin K (the antidote for warfarin) were unsuccessful in reversing or even improving her coagulation parameters. For days she continued to have large bloody bowel movements. Recombinant human Erythropoietin was started at 10,000 units daily. Over the next 5 days the bleeding completely stopped. On a maintenance treatment for several weeks she did not rebleed and her Hemoglobin remained stable. No blood transfusion was needed, over the following months despite markedly abnormal coagulation parameters. No side effects were noted. Example no. 11: is a 35 year old female, with chronic renal failure due to diabetic nephropathy, who complained of fatigue, and weakness. She had chronic excessive menstrual blood loss and a Hemoglobin of 9.1. Low dose Erythropoietin −2000 U was administered two times a week, than weekly, than every other week. The patient reported a significant reduction in the menstrual blood loss and an improvement in her sense of well being. Her Hemoglobin increased to 11.4 and remained stable at that level. During the subsequent months of follow up, Erythropoietin was discontinued. The blood loss and Hemoglobin remained stable(Hemoglobin=11.4). No side effects were noted.

The superficial bleeding of the skin or mucosa may also be decreased or stopped by the topical administration of Erythropoietin on the bleeding skin or mucosa using known vehicles for topical administration of medication in order to decrease or stop the bleeding. In the case of bleeding from the gastrointestinal mucosa, besides the methods of administration previously mentioned, Erythropoietin can be administered orally, as an enema, or the bleeding segment of bowel can be lavaged with a solution containing Erythropoietin, in order to decrease or stop the bleeding.

These examples showed a clear and unexpected benefit in using Recombinant human Erythropoietin as a hemostatic agent. It is particularly but not exclusively suited for severe, chronically recurrent bleeding conditions, which failed local attempts to stop the bleeding and where repeated transfusions of blood products (red blood cells, platelets, plasma, coagulation factors) could not stop the bleeding. It is also suited in localized or diffuse bleeding as an initial treatment or at any time during the course of treating the bleeding conditions. The effectiveness of Recombinant human Erythropoietin as a hemostatic agent (stopping severe bleeding) is demonstrated by its effectiveness while the patient is receiving Recombinant human Erythropoietin, and the recurrence of bleeding upon cessation of Recombinant human Erythropoietin (see example no. 2). Also, its effect in stopping the bleeding in patients with bleeding disorders or who are on an overdose of anticoagulant plus an antiplatelet agent (see example no. 1) is proof of its boosting effect on the various mechanisms involved in hemostasis.

Recombinant human Erythropoietin provides a conservative treatment for bleeding conditions for which there was no good treatment, conservative or surgical. Patients who were completely transfusion dependent, had repeated surgical/nonsurgical attempts to stop the bleeding and were repeatedly hospitalized, after the administration of Recombinant human Erythropoietin became totally transfusion independent, and no hospitalization or surgical procedures were needed. The patients who were already admitted to the hospital for severe bleeding were started on Recombinant human Erythropoietin in the hospital and were discharged shortly thereafter to continue their treatment as outpatients. But most frequently admission was avoided altogether and the treatment was administered entirely as outpatient. The patients returned to an excellent quality of life. There was a major saving in the patient's healthcare cost. No side effects were noted. Recombinant human Erythropoietin can be used prior to, during or after surgery to avoid excessive bleeding in patients with abnormal hemostasis or on anticoagulants/antiplatelet drugs. Also it can be used in patients with a lesion likely to bleed (such as vascular abnormalities, malignant lesions, etc.). This new use of Recombinant human Erythropoietin beyond the anemia of chronic renal failure, anemia of HIV infected patients, anemia of cancer, as a "hemostatic agent" provides a new and significant medical advance in the treatment of bleeding patients.

The method of administration of Erythropoietin for the treatment of bleeding from the gastrointestinal mucosa may be chosen based upon the location of the bleeding segment. In order to most directly reach the bleeding segment, the Erythropoietin may be administered orally, as an enema, as a suppository or by lavaging the bleeding segment of a bowel with a solution containing Erythropoietin.

As an emergency treatment for limiting the extent of bleeding in patients with bleeding injuries such as gun shot wounds, work related injuries, or other accidental injuries until appropriate medical care is available an emergency kit may be prepared containing self injectable syringes prefilled with the appropriate dosages of Erythropoietin, which the injured person or someone next to him would inject subcutaneously as soon as possible after the accident occurred. This could limit the extent of blood loss and greatly influence the initial course of events in bleeding injuries. This use could be beneficial in combat situations, at work related accidents or traffic accidents etc. If the bleeding continues Erythropoietin can be continued until complete resolution of bleeding is accomplished.

In general, in view of the present discoveries, Recombinant human Erythropoietin should be considered as a "hemostatic agent" extending beyond its present indication for boosting hemopoesis.

Although the invention has been described in terms of preferred embodiments and specific examples, it is expected that the invention may be practiced by modifications that persons skilled in this art may achieve. Accordingly, the invention is to be understood as what is described in the following claims.

I claim:

1. A method for treating an individual patient bleeding from an organ or body part having benign or malignant lesions, comprising administering to the individual effective doses of Recombinant human Erythropoietin so that the bleeding is stopped or significantly reduced.

2. A method for enhancing hemostasis by administering to the individual effective doses of Recombinant human Erythropoietin so that the bleeding is stopped or significantly reduced.

3. A method for treating an individual patient bleeding from an organ or body part having benign or malignant lesions, comprising administering to the individual effective doses of Recombinant human Erythropoietin so that the bleeding is stopped or significantly reduced, wherein the organ or body part, has surgical, traumatic or difficult to heal lesions.

4. The method of claim 1 wherein the individual has congenital or acquired vascular abnormalities.

5. A method for treating an individual patient bleeding from an organ or body part having benign or malignant lesions, comprising
administering to the individual effective doses of Recombinant human Erythropoietin so that the bleeding is stopped or significantly reduced, wherein the individual has radiation injury.

6. A method for treating an individual patient bleeding from an organ or body part having benign or malignant lesions, comprising
administering to the individual effective doses of Recombinant human Erythropoietin so that the bleeding is stopped or significantly reduced, wherein the individual is bleeding from an organ transplant or skin graft.

7. The method for treating bleeding of claim 2, wherein individuals who have normal as well as abnormal hemostasis and normal as well as abnormal coagulation, are administered Recombinant human Erythropoietin in order to reduce, stop or prevent the bleeding altogether.

8. A method for treating an individual patient bleeding from an organ or body part having benign or malignant lesions, comprising
administering to the individual effective doses of Recombinant human Erythropoietin so that the bleeding is stopped or significantly reduced, where patients are HIV positive.

9. The method for treating bleeding of claim 1 in which Recombinant human Erythropoietin is administered subcutaneously, intravenously or orally.

10. The method for treating bleeding of claim 9 in which Recombinant human Erythropoietin is administered subcutaneously.

11. A method for treating an individual patient bleeding from an organ or body part having benign or malignant lesions, comprising
administering to the individual effective doses of Recombinant human Erythropoietin so that the bleeding is stopped or significantly reduced, in which human Recombinant human Erythropoietin is administered during an initial treatment in dosages between 15,000 to 140,000 units per week until the bleeding stops, and is then continued to be administered on a reduced basis thereafter.

12. The method for treating bleeding of claim 11, in which the dose of Recombinant human Erythropoietin is adjusted to the individual patient depending on the severity of bleeding, the status of the hemostatic and coagulation parameters and the severity of anemia, in order to stop the clinical signs of bleeding and to maintain a stable Hemoglobin/Hematocrit.

13. The method of treating bleeding of claim 11 in which the "maintenance dose" is 6,000 units–35,000 units per week, adjusted to the individual patient in order to control the signs of clinical bleeding, to maintain a stable Hemoglobin and Hematocrit and prevent rebleeding.

14. The method for treating bleeding of claim 13, wherein the individual is placed on long term maintenance dosages of Recombinant human Erythropoietin injection of 4,000–20,000 units per month during which treatment the patient is monitored for clinical signs of bleeding and the Hemoglobin/Hematocrit determined.

15. The method of treating the bleeding of claim 14 wherein the patient, if he or she stopped bleeding during the long-term maintenance treatment, is monitored closely without the administration of Recombinant human Erythropoietin, during a long term follow up period.

16. The method of treating bleeding of claim 11 wherein the administration of Recombinant human Erythropoietin during the initial treatment of bleeding takes place daily, two times a week or three times a week.

17. The method of treatment of bleeding of claim 11 wherein the initial treatment is usually administered for 1–2 weeks until the bleeding is under control.

18. The method of treatment of bleeding of claim 13 wherein the maintenance treatments two or three times per week, adjusted to the patient's needs, during which time the patient is monitored for evidence of recurrent bleeding.

19. The method of treatment of bleeding of claim 13 wherein the maintenance treatment lasts about 4–6 weeks, adjusted to each individual patient, in order to keep the patient free of bleeding.

20. The method of treating bleeding of claim 14 wherein the long term maintenance doses of Recombinant human Erythropoietin are administered at 1,2,3 or 4 weeks interval adjusted to each individual patient in order to maintain the patient free of bleeding.

21. The method of treatment of bleeding of claim 14 wherein the long-term maintenance treatment lasts for several weeks, months or years depending on each individual patient and on the reoccurrence or not of signs of bleeding.

22. The method of treatment of bleeding of claim 14 wherein patients who completely stopped bleeding during the long-term maintenance treatment should be monitored indefinitely with long term follow up during which no Recombinant human Erythropoietin is administered.

23. The method of treating bleeding of claims 18 wherein a patient who rebleeds during any phase of the treatment, will be switched to an initial treatment regimen if the bleeding is severe, or to a maintenance treatment for less severe bleeding.

24. A method for treating bleeding in patients with lesions that bleed excessively in patients with hemostatic or coagulation abnormalities, or patients on anticoagulants/antiplatelet drugs for other coexistent conditions, comprising the concomitant administration of effective doses of Recombinant human Erythropoietin with the anticoagulant/antiplatelet drug.

25. The method for treating bleeding of claim 24 where the lesions are vascular abnormalities, malignant lesions, or radiation injuries.

26. The method of treating bleeding of claim 1 in which patients already on 10,000 units of Recombinant human Erythropoietin intravenously 3 times a week, are switched during the initial treatment to 15,000 to 20,000 units of Recombinant human Erythropoietin daily subcutaneously for the purpose of stopping the bleeding.

27. The method of treating bleeding of claim 26, wherein the patients have chronic renal failure patients on hemodialysis.

28. The method of treating bleeding of claim 26, wherein after the bleeding has completely stopped, the patient can be switched back during the maintenance treatment to their dose of 10,000 units of Recombinant human Erythropoietin given intravenously 3 times a week.

29. The method of treating bleeding of claim 1, whereby the bleeding patient is on intravenous Recombinant human Erythropoietin, and the Erythropoietin is administered during an initial treatment subcutaneously until the bleeding stops, after which Recombinant human Erythropoietin is switched back during the maintenance treatment to be administered intravenously.

30. The method of bleeding of claim 29, wherein the patient has chronic renal failure and is on hemodialysis.

31. The method of administering Recombinant human Erythropoietin prophylactically or therapeutically to patients with anemia who cannot be transfused and who need surgery comprising administering an effective amount of Recombinant human Erythropoietin during and after surgery in order to minimize the blood loss.

32. The method of administering Recombinant human Erythropoietin to patients undergoing surgical procedures which require infusion/perfusion with an anticoagulant simultaneously with the surgical procedure, increasing the risk of bleeding, comprising administering an effective dose of Recombinant human Erythropoietin before, during and after the surgical procedure in order to limit the blood loss.

33. The method for treating bleeding of claim 1 wherein a bleeding segment of the body or organ is perfused with Recombinant human Erythropoietin through the afferent blood vessel to stop the bleeding.

34. The method of treating bleeding from the gastrointestinal mucosa by the administration of Erythropoietin orally, as an enema, or as a suppository or lavaging the bleeding segment of a bowel with a solution containing Erythropoietin, depending on the bleeding segment in order to decrease or stop the bleeding.

35. A method for treating an individual patient bleeding from an organ or body part having benign or malignant lesions and a low platelet count and low Hemoglobin level, comprising increasing the individual's platelet count and Hemoglobin level and stopping or significantly reducing bleeding by administering to the individual effective doses of Recombinant human Erythropoietin by subcutaneous, intravenous or oral administration.

* * * * *